United States Patent
McIntyre et al.

(10) Patent No.: US 9,879,219 B2
(45) Date of Patent: Jan. 30, 2018

(54) METHOD OF PRODUCING A CHITINOUS POLYMER DERIVED FROM FUNGAL MYCELIUM

(75) Inventors: Gavin McIntyre, Troy, NY (US); Eben Bayer, Troy, NY (US); Daniel Flagg, Schenectady, NY (US)

(73) Assignee: Ecovative Design, LLC, Green Island, NY (US)

( * ) Notice: Subject to any disclaimer, the term of this patent is extended or adjusted under 35 U.S.C. 154(b) by 1017 days.

(21) Appl. No.: 13/411,877

(22) Filed: Mar. 5, 2012

(65) Prior Publication Data

US 2012/0227899 A1    Sep. 13, 2012

Related U.S. Application Data

(60) Provisional application No. 61/464,740, filed on Mar. 7, 2011.

(51) Int. Cl.
*C12N 1/00* (2006.01)
*A61K 36/06* (2006.01)
*C12N 1/14* (2006.01)

(52) U.S. Cl.
CPC ..................... *C12N 1/14* (2013.01)

(58) Field of Classification Search
None
See application file for complete search history.

(56) References Cited

U.S. PATENT DOCUMENTS

| | | | | |
|---|---|---|---|---|
| 3,317,375 A | * | 5/1967 | Molinet et al. | 514/580 |
| 5,854,056 A | * | 12/1998 | Dschida | 435/254.1 |
| 2008/0145577 A1 | * | 6/2008 | Bayer et al. | 428/35.6 |
| 2009/0307969 A1 | * | 12/2009 | Bayer et al. | 47/1.1 |

FOREIGN PATENT DOCUMENTS

EP    0226292 B1 * 10/1986

OTHER PUBLICATIONS

Sundari et al., Biotechnology Techniques, vol. 13, p. 491-495, 1999.*
Agnese et al. (The 37th Annual Meeting and Exposition of the Controlled Release Society, Jul. 2010, Portland, Oregon, U.S.A.*

* cited by examiner

*Primary Examiner* — Chris R Tate
*Assistant Examiner* — Douglas F White
(74) *Attorney, Agent, or Firm* — Francis C. Hand; Carella, Bryne, et al.

(57) ABSTRACT

The process of growing a homogeneous polymer matrix comprising the steps of growing a viable mycelium in a liquid suspension; extracting mycelium from the liquid suspension; thereafter incubating the mycelium for a period of time sufficient to induce mycelium cohesion and to form a solid material; and thereafter drying the solid material to remove moisture and to inactivate the mycelium.

20 Claims, 9 Drawing Sheets

METHOD OF PRODUCING A CHITINOUS POLYMER DERIVED FROM FUNGAL MYCELIUM

This application claims priority of Provisional Patent Application 61/464,740 filed Mar. 7, 2011.

This invention relates to a method of producing a chitinous polymer derived from fungal growth.

As is known from published United States Patent Application 2008/0145577 use can be made of a fungus to form composite materials by mixing an inoculum including a preselected fungus with discrete particles and a nutrient material capable of being digested by the fungus. It is also known from U.S. Pat. No. 8,001,719 to enclose and grow a fungal primordium in a mold to obtain a mass of fungal tissue in the form of low density chitinous material.

It is an object of this invention to provide a improved method for the production of chitinous materials.

It is another object of the invention to provide a method for the growing of a homogeneous polymer matrix.

It is another object of the invention to provide a material to replace synthetic plastic materials, particularly, for packaging purposes.

Briefly, the invention provides several methods of growing a homogenous polymer matrix that is comprised predominately of fungal chitin and trace residues (beta-glucan, proteins). The resultant material is a rigid, high-density amorphous polymer that can serve in applications that are currently served by synthetic plastics.

The fungal mycelium, the precursor material, can be cultivated in either batch or continuous processes and the mycelium can either be extracted from a growth media or the tissue can be grown in sheets that are of usable dimensions. The extracted tissue culture can be preprocessed (homogenized, blended, hammer milled, etc) in order to achieve a uniform size prior to injection molding or forming. Mycelium sheets can be processed via cutting (knife, water jet, laser, die cut, punching, or any other suitable technique) to obtain two-dimensional features, or individual sheets can be stacked and grown together to form three-dimensional features.

The mycelium is preprocessed, in either suspended masses or sheets, processed (injection molded, compressed into a cavity, and the like), and then incubated (90% RI-I, 30° C.) to induce mycelium cohesion and result in a uniform solid. The resultant solid, a homogenous mass of mycelial chitin, is then dried using forced convection or conduction to inactivate the fungus and prevent further growth.

Mycelium Pellets

If the mycelium is extracted from a growth media, such as a gelatinous suspension, the tissue can be separated either mechanically (filtration, skimming, centrifuging, etc) or chemically (isopropyl alcohol, ethanol, etc). The mycelium fragments, or pellets, can then be injected, vibrated, or mechanically applied into an incubation enclosure while animate. The fragments can then be either incubated in a tool or ejected and incubated in a secondary growth environment to promote various growth morphologies and physiologies of the fungal tissue. A supplemental particle, gelling agent, or fiber can be used to carry additional nutrition (trace minerals: $CaCl_2$, $MnSO_4$, $K_2HPO_4$; maltodextrin, peptone, and the like), or serve as scaffolding for enhancing mycelium strength.

In another embodiment, the mycelia tissue is applied to a form or mold and bound using the application of heat, pressure, or both. Extracted mycelia fragments my also be bound through the use of other chemical post-processes.

Mycelium Sheets

Mycelium will naturally grow across the surface of a nutrient rich fluid or solid (reference: Dschida). The mycelium sheets, when grown on a fluid (nutrient broth, alginate suspension) or a solid-liquid boundary (woven or matt fiber on nutrient broth), can be extracted while viable for thin film applications.

Similarly, the mycelium sheets can be post processed (cut, pressed) to graft desired two-dimensional features on individual sheets. The individual sheets can be stacked, with or without additional support material, to form three-dimensional solids. Additional fibers or particles can be applied to the sheets to enhance physical performance in various loading scenarios (woven fiber to bolster tensile strength, particles to enhance compressive strength). All processing can occur with the mycelium still viable, and can grow together via thigotropism and zygotropism (heterothallistn/homothallism).

Other Processing

In order to transport the viable mycelia material, or to preserve the active tissue for an extended period, additional post processing steps can be taken to maintain an active culture. Some methods include, but are not limited to, freeze drying, dehydrated, cryogenically freezing, or transported on a secondary carrier (particle or fiber).

Process Steps:

1) Grow sufficient quantities of viable mycelium in a liquid suspension.
   a. Growth environment is maintained such that mycelia tissue creation is maximized.
   b. Growth environment may be modulated, by changing the fluid viscosity, particle or fiber presence, nutrients, ph, temperature, dissolved gas concentration, and agitation method, to control the quantity and type of mycelium that is created. Key characteristics that may be modulated through these variables include cell wall thickness and composition, branching frequency, hypha expression (Skeletal, generative, and the like), and specific enzyme production.
2) Extract viable mycelium from the liquid culture.
   a. Mycelium may be extracted in-situ by either mechanical methods (filtration, skimming, centrifuging, etc) or chemical methods (isopropyl alcohol, ethanol, etc).
   b. Mycelium may be extracted in a bulk format by allowing sheets to form between the liquid-gas boundaries on the surface of the media.
   c. Mycelium may also be extracted in a continuous fashion by passing a porous membrane material through the culture, allowing the mycelium to adhere and grow along the membrane.
3) Process extracted mycelium. Mycelium, once extracted, can be processed into a number of forms for further processing steps. These forms include:
   a. Pellets or fragments, which can be injected, pressed, vibrated, or formed into bulk two or three dimensional shapes. Pellets or fragments that can be batch or continuously deposited into a non-woven sheet, extruded into a profile, or foamed into a lightweight material.
   b. Sheets, which can be sliced, stacked, woven, rolled, folded, or formed to produce a wide variety of two and three-dimensional shapes. Multiple sheets may be combined together to produce thicker sections or thicker objects. Generally, sheets self adhere due to the growth properties of the mycelium, but they may also be adhered through the application of heat, pressure, or chemical additives.

4) Incubate processed and formed mycelium
   a. Processed and formed mycelium may be allowed to incubate such that the mycelium self adheres on hyphae-hyphae level to produce a strong contiguous connection between the previously disaggregated particles, pellets, sheets, or other fragments
   b. In some cases processed and formed mycelium may be immediately heated, pressed, or chemically adhered.
5) Dry resulting mycelium product
   a. In this step the now formed composite material is dried to remove moisture and inactivate the mycelium.

These and other objects and advantages of the invention will become more apparent from the following detailed description taken in conjunction with the accompany drawings wherein.

Figure 8:
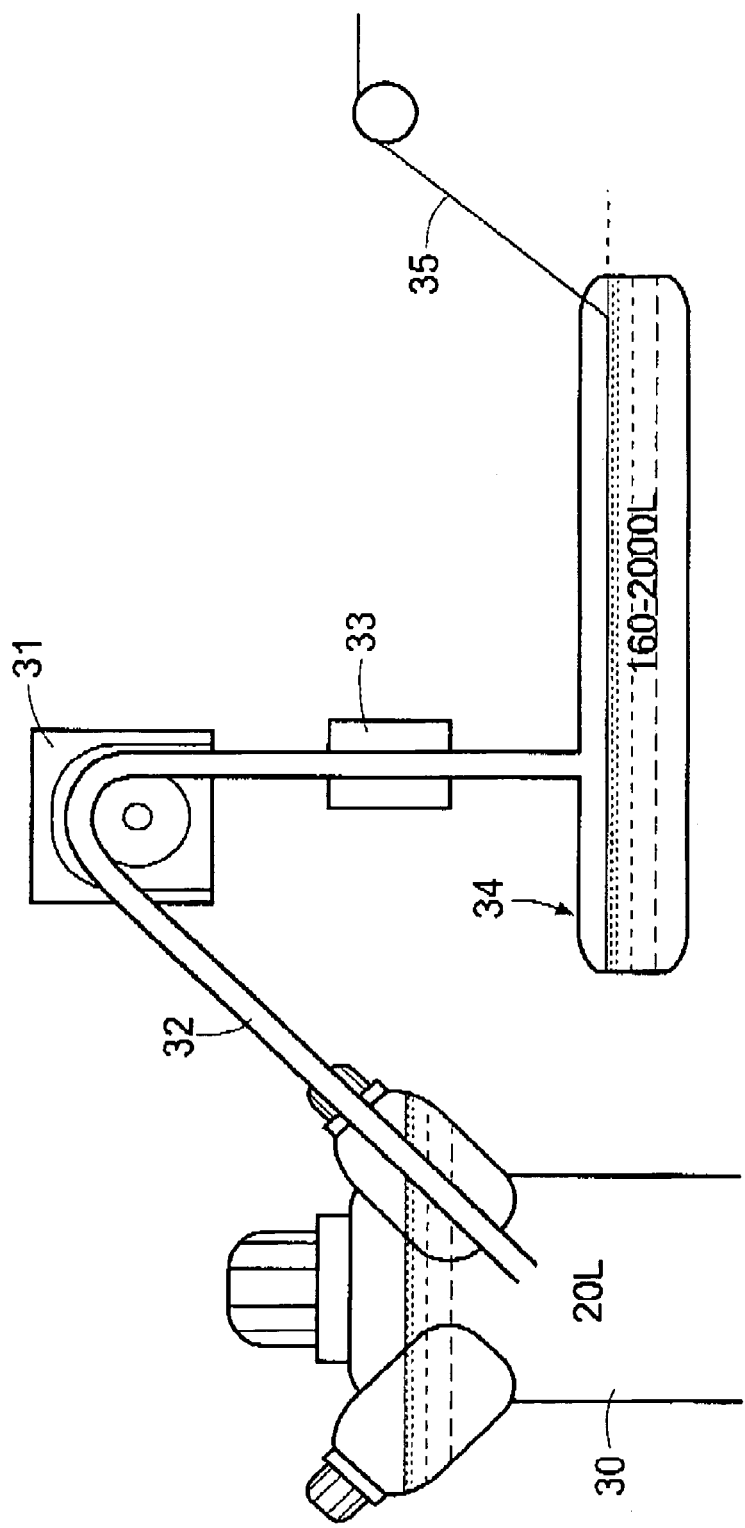
Figure 9:
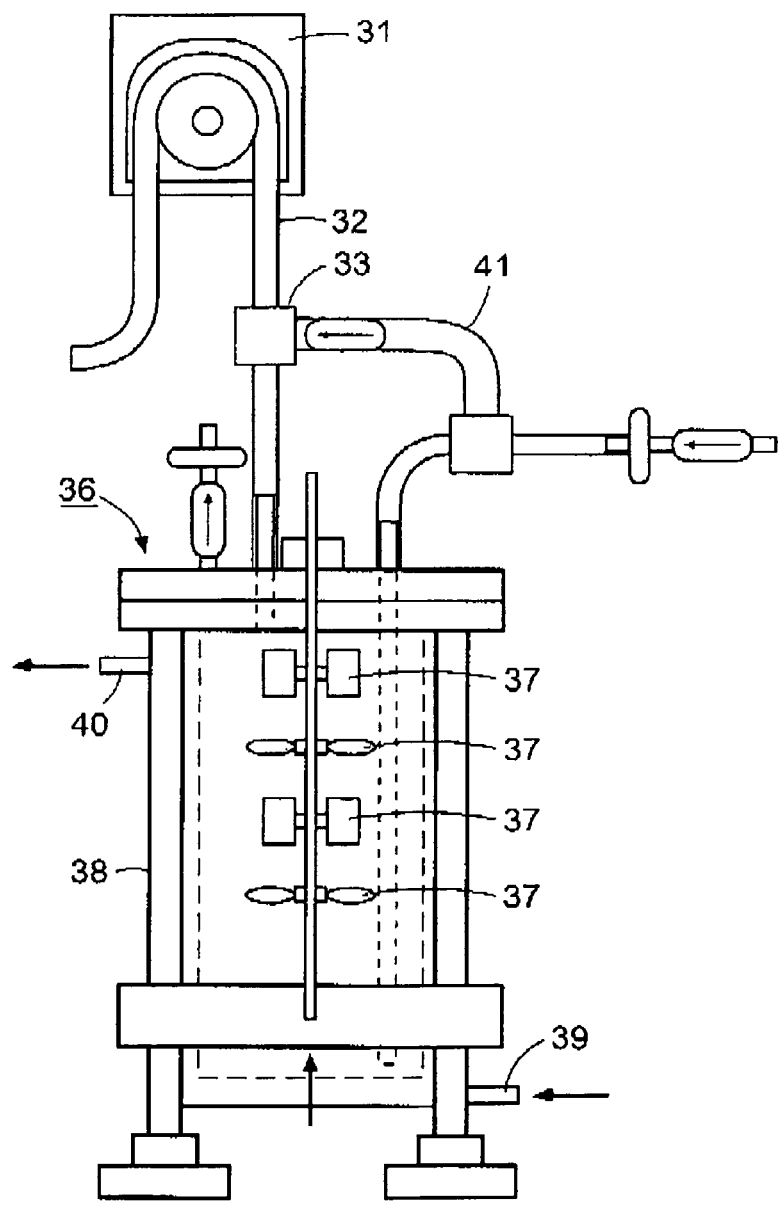
Figure 10:
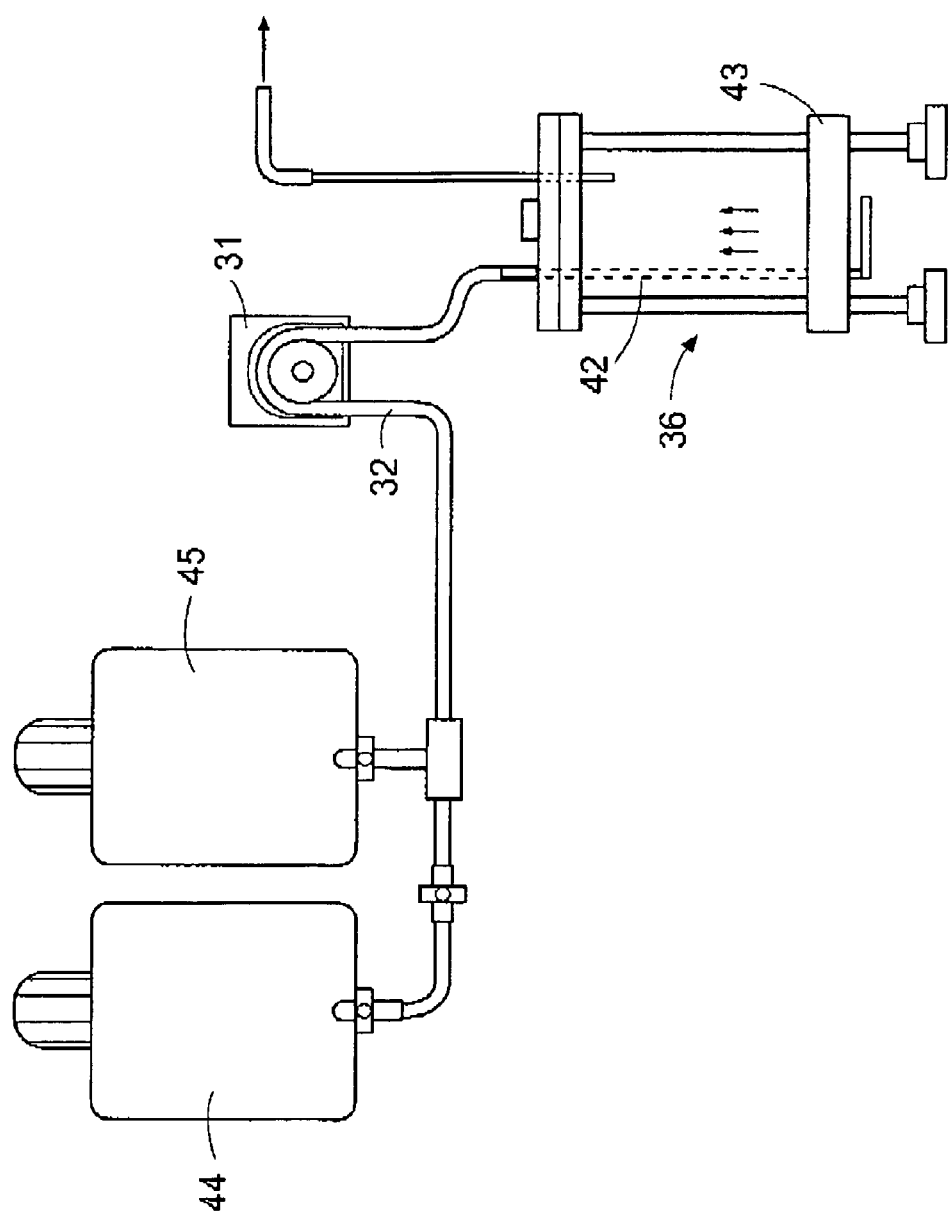
Figure 11:
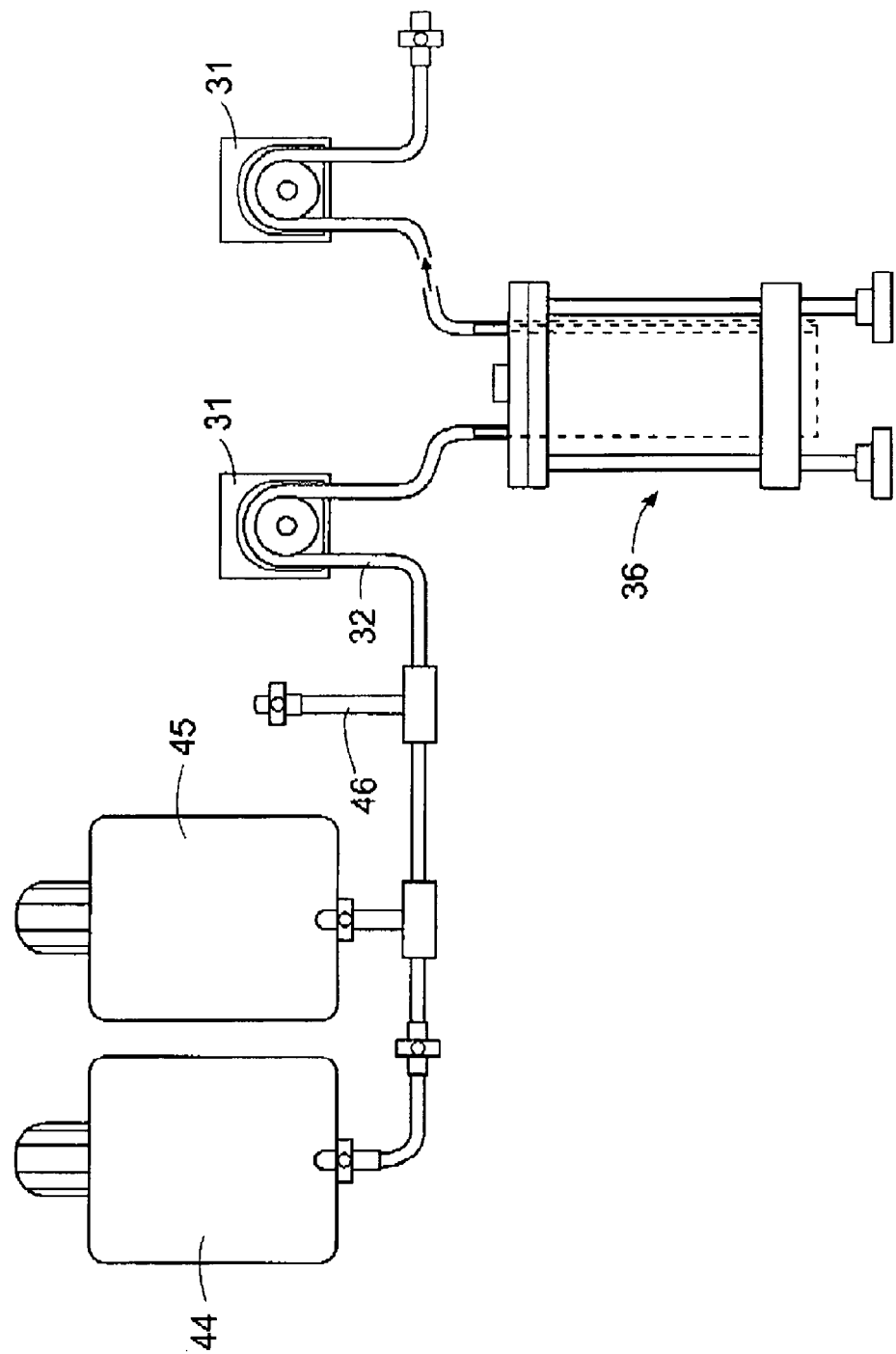
Figure 12:
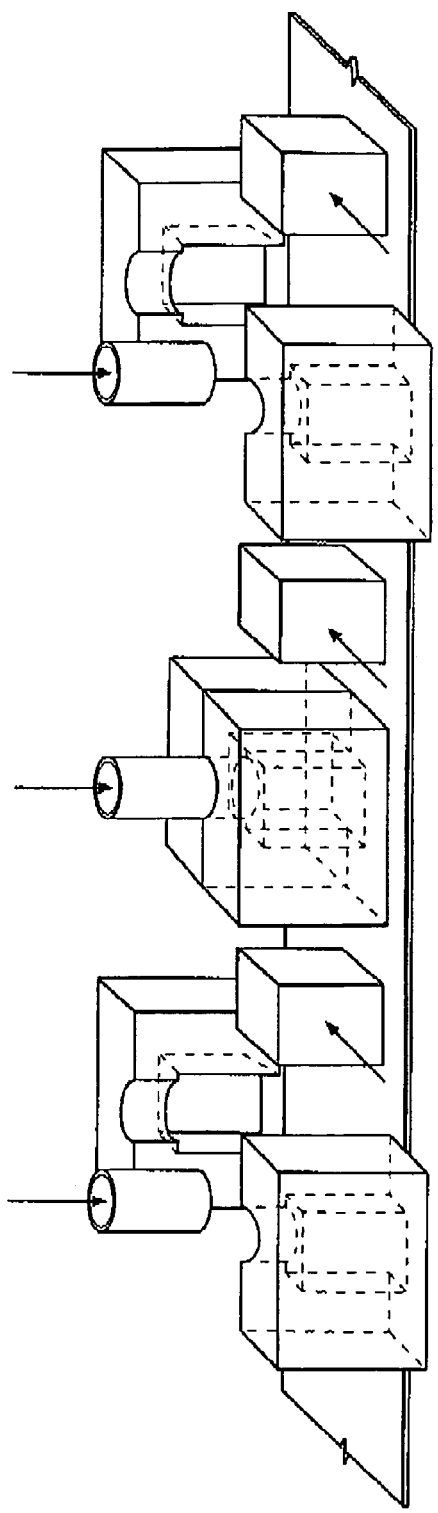
Figure 13:
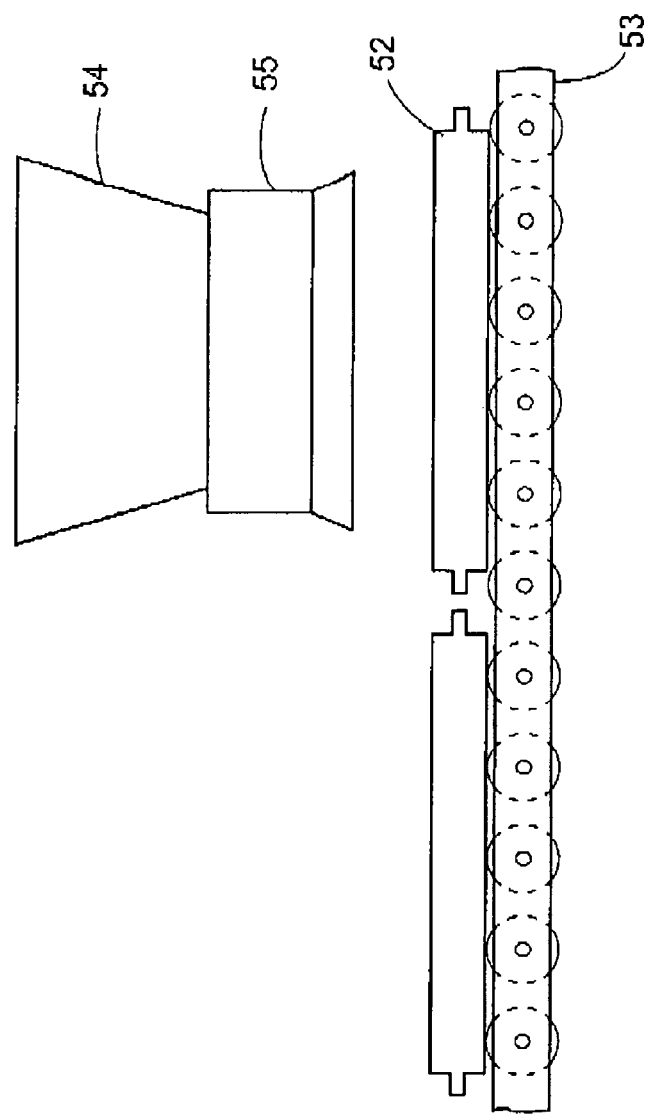

FIG. 8 schematically illustrates a view of a production line for producing a mycelium sheet in accordance with the invention;

FIG. 9 schematically illustrates a view of a production facility for producing an aerated mycelium product in accordance with the invention;

FIG. 10 schematically illustrates a view of another production facility for producing a mycelium product in accordance with the invention;

FIG. 11 schematically illustrates a view of another production facility for producing a mycelium product in accordance with the invention;

FIG. 12 schematically illustrates a view of another production facility for producing multiple mycelium products in accordance with the invention; and FIG. 13 illustrates a schematic view of a part of another production facility for producing mycelium products on a continuous basis.

The following examples show the manner in which the invention is exercised.

EXAMPLE 1

1. A nutrient broth is mixed in a one liter media bottle and consists of 21.4 g Maltodextrin, 1.2 g $CaCl_2$, 1.2 g Nutritional Yeast, 2.0 g agar agar, 0.8 g $MgSO_4$, 0.8 g $MnCl_2$, 0.032 g $CuSO_4$, and 660 mL tap water.
2. The solution is heated to 90° F. and stirred using a magnetic stir rod and plate.
   Once the media has met an even consistency the solution is poured into 600 mL beakers in 20 mL increments. The beakers are covered with aluminum foil and compressed around the perimeter of each vessel.
3. A one-liter stainless steel Eberbach blender is filled with 500 mL of municipal tap water. The beakers and the blender are sterilized in an autoclave at 15 psi and 240° F.
4. Once removed, the vessels are allowed to cool to room temperature in a HEPA filtered laminar flow hood.
5. A culture of a filamentous fungus, a 100 mm diameter Petri dish culture, is applied to the Eberbach and homogenized by blending the tissue into 1 mm2 fragments.
6. Using a 2:1 ratio (media:tissue), 10 mL of the blended tissue culture is applied to each beaker an then recovered. The media bottles are incubated for five to nine days in a 90% RH and 86° F.

The following process steps reflect two methods of creating a chitinous mycological polymer:

7. Following the incubation cycle, the fungal mycelium is extracted.
   a. The mycelium sheet that forms across the surface of the nutrient broth is extracted, and the exposed broth is recovered to allow for an additional mycelium sheet to grow. This process can be repeated three times before the nutrients are consumed.
   b. The broth with the mycelium sheet is homogenized using a blender, and the broth is then filtered through 0.45 μm vacuum filter. A diaphragm pump separates the nutrient media into a containment vessel, the air is circulated through the pump, and the viable mycelium is collected at the filter. The broth can be enriched for reuse or discarded.
   c. The broth is mixed with isopropyl alcohol at a 25% concentration [v:v], which separated the mycelium from the nutrient broth.
8. The fungal mycelium can then be processed, with each sub-example relating to the extraction process in (7).
   a. The extracted sheets are placed in direct contact with one another and then incubated for an additional three days in a 90% RH and 86° F. environment. The fungal mycelium sheets will now fuse into a cohesive whole through zygotropism. Another process leveraging the mycelium sheets entails forming the sheet(s) over a buck or negative form, and then dried on the tools to grant form.
   b. The separated mycelium is injection molded, with or without supplemental carrier particles, into a two or three part enclosure and then ejected from the form. The fluid is metered using a peristaltic pump that is conveying the gelatinous fluid at a flow rate of 50 mL per minute. The mycelium fragments are incubated for an additional three days in a 90% RH and 86° F. environment. The fungal mycelium sheets will now fuse into a cohesive whole through zygotropism.
   c. Chemically separated mycelium can be used in a similar manner to (8b).
9. The final step is to dry the mycelium mass with forced convection, either with a designed in contraction factor (65%) or with a drying fixture to maintain dimensional stability. The material can also be dried with conduction, using a heated buck and collar.

Figure 1:
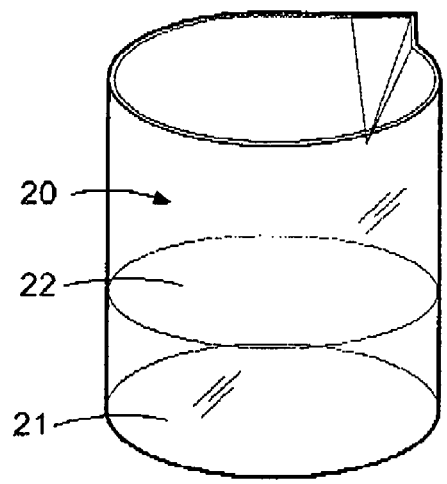
FIG. 1 illustrates a perspective view of a beaker in which mycelium colonies are cultivated on a liquid media in accordance with the invention.

Referring to FIG. 1, use may be made of a beaker 20 for cultivating mycelium colonies on a liquid media 21 either to form a sheet 22 of a specific geometry (i.e. circular as shown) or into a general configuration that can be post processed.

In a second stage incubation, multiple sheets 22 may be stacked potentially in a specialized environment to induce various morphological characteristics. The sheets fuse together via homothallic or heterothallic zygotropism. The number of sheets and growth enclosure geometry are defined by the final required dimensions accounting for contraction.

Subsequently, in a third step, homogenous chitin polymer post drying is performed. Remaining water is removed and the fungus is rendered inanimate. Material can be chemically post processed to retain hydrophobicity, increase elasticity or stiffness, and the like.

Figure 2:
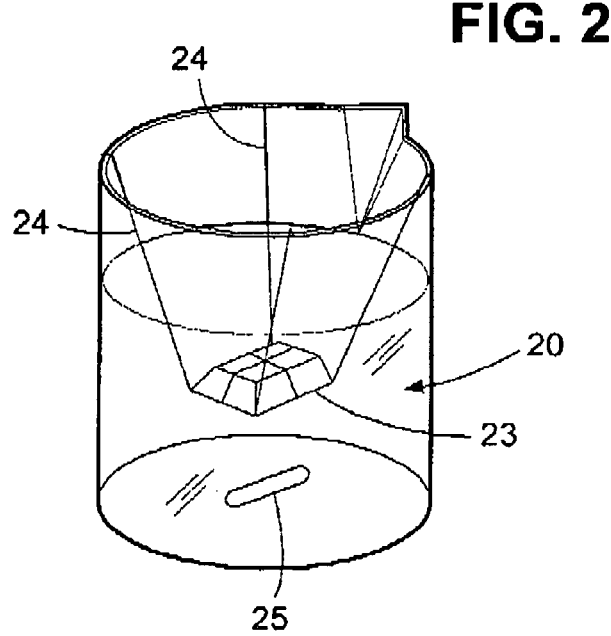
FIG. 2 illustrates a perspective view of a beaker in which mycelium colonies are to be cultivated on a suspended scaffold in accordance with the invention.

Referring to FIG. 2, wherein like characters indicate like parts as above, use may be made of a scaffold 23 constructed from a rigid, water insolvable, digestible or non-digestible matrix (woven jute, mineral, agar, metal wire, and the like). The scaffold 23 may be embedded with secondary materials (conductive).

In use, the scaffolding 23 is immersed in broth that contains tissue culture and propagating nutrients. As illustrated, the scaffold 23 is suspended by wires 24 into the interior of the beaker 20 for immersion in the broth.

Figure 3:
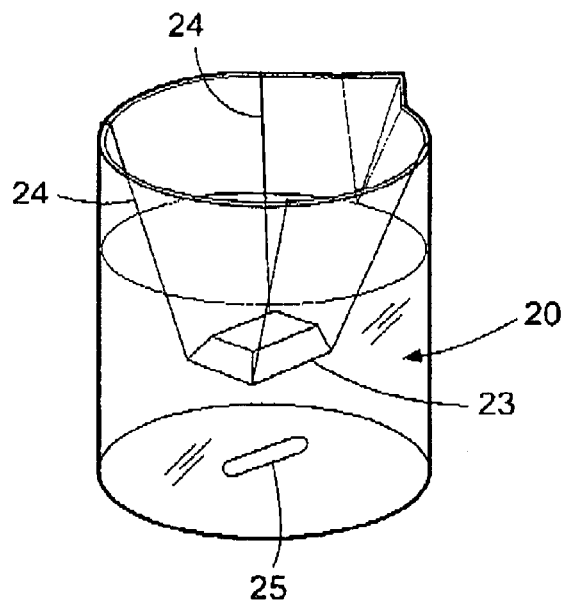
FIG. 3 illustrates a perspective view of the beaker of FIG. 2 after the mycelium colonies have been cultivated on a suspended scaffold in accordance with the invention.

After immersion of the scaffold 23, the broth is agitated by a magnetic stir rod 25 and/or aerated. During this time, mycelium grows onto and potentially digests the scaffold 23 to obtain net geometry comprised of fungal polymer as indicated in FIG. 3. Thereafter, the mycelium mass is extracted from the broth and incubated at high humidity to induce the production of hydrophobin. Next, the mass is slowly convective dried to obtain the finished material.

Alternatively, the scaffold 23 may be placed in intimate contact with a mycelium sheet 22 (not shown) post colonization. In this embodiment, the mycelium colonizes with contact with the scaffold 23.

Figure 4:
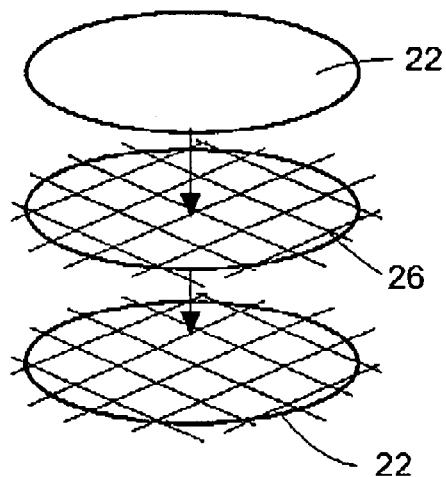
FIG. 4 illustrates an exploded view of a stacked array of a mycelium sheet and textile layers for forming a final product.

Referring to FIG. 4, one or more mycelium sheets 22 can be combined with natural or synthetic. woven or matt textiles 26 that are sterilized and saturated with water (jute, coir, etc). Fibers are either applied under stress or at steady state.

The textiles 26 may be stacked adjacent to each other and, where woven, may be laid up in varying directions, i.e. with the threads of one woven textile at an angle other than 90° relative to the threads of the adjacent woven textile.

Figure 5:
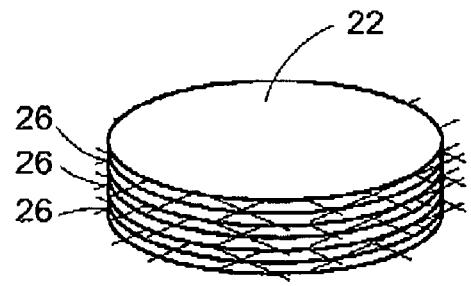
FIG. 5 illustrates a perspective view of a product formed of a stack of mycelium sheets and textile layers in accordance with the invention.

Referring to FIG. 5, a multiple number of mycelium sheets 22 and a multiple number of textiles 26 may be stacked and incubated until these components compose a uniform solid. As above, the surfaces of the resulting solid may be post processed for hydrophobicity or antimicrobial properties.

Figure 6:
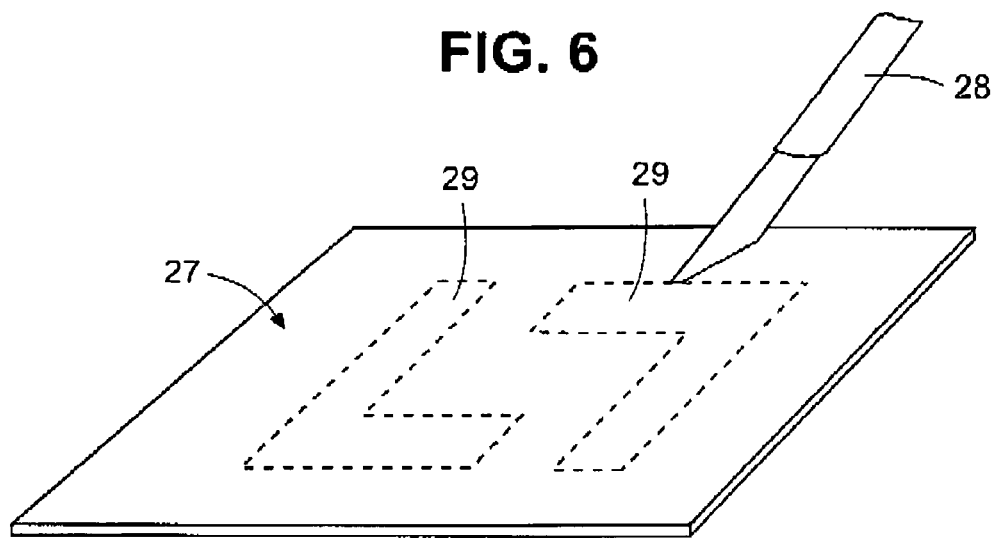
FIG. 6 illustrates a manner of removing a predetermined shape from a mycelium sheet.

Referring to FIG. 6, a mycelium sheet 27 may be grown to a predetermined geometry, dependent upon the scale and geometry of the near net part as described above. The resulting tissue is then dehydrated via forced convection and the fungus is inactivated. Similarly, the sheet 27 can be refrigerated to reduce the organism's metabolism. The sheet 27 can then be reanimated by either allowing the sheet 27 to acclimate to room temperature or by adding moisture (% RH, water, $H_2O$).

The mycelium sheet 27 may be cut by a suitable stylus 28 to form cutouts 29 of predetermined shape or shapes. As illustrated, the mycelium sheet 27 is cut to obtain two L-shaped cutouts.

Figure 7:
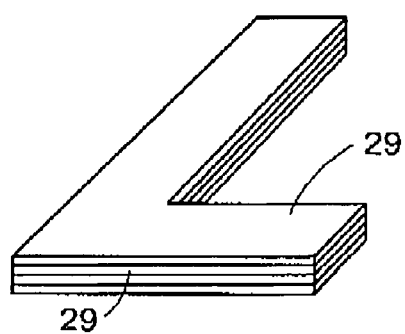
FIG. 7 illustrates a perspective view of a product formed of a stack of shapes removed from one or more mycelium sheets in accordance with the invention.

Referring to FIG. 7, a plurality of cutouts 29 from one or more mycelium sheets 27 are stacked to create the final three dimensional mycelium part. Municipal water is used to saturate the dehydrated sheets and to reanimate the organism, this can occur before or after cutting the sheets 27.

Water and/or glycol may be added to the stack of cutouts 29 to plasticize the tissue. Inhibiting and promoting chemicals/environmental stimuli may be added to navigate growth patterns.

Once the mycelium cutouts 29 fuse together forming a cohesive whole, the biomaterial is dried to cause cell death (convective heat, radiation, osmotically). A fixture can be used to maintain dimensional stability, such as a weighted wire mesh.

Of note, a salt solution will osmotically dry the part partially and can embed ions into the cell wall/matrix. This can grant conductivity thermal and electrical, for example, to the final mycelium part and/or chemically alter the functional groups of the fungal cell wall.

Anti-fungal chitosan can be created by heating the part and adding NaOH.

Disulphide bonds can be used to strengthen the surface and enhance hydrophobicity.

Referring to FIG. 8, in order to form a continuous mycelium sheet 30, a broth as described above is place in a beaker 30 of, e.g. 20 liter size, that is slowly rotated during cooling for a period of growth of 9 days. Thereafter, the resultant material is pumped out of the beaker 30 via a peristaltic pump 31 through a through a tube 32 and homogenizer 33 and into one or more tanks or troughs 34, e.g. having a capacity of from 160 to 2000 liters, for a period of growth of from 3 to 9 days. Thereafter, a sheet 35 of mycelium is removed from the media fluid line in each tank for further processing.

Referring to FIG. 9, wherein like reference characters indicate like parts as above, a sterilized media may be metered by a peristaltic pump 31 through a large ID Viton tube 32 via a homogenizer 33 into a vessel 36.

The vessel 36 is equipped with a plurality of impellers 37 within a chamber thereof that rotate at a low RPM to mix and agitate the cooling fluid in the chamber to evenly distribute the media components. In addition, a jacket 38 surrounding the inner chamber of the vessel 36 has an inlet 39 for a supply of chiller fluid and an outlet 40 for expelling the chiller fluid. The jacket 38 is chilled with gravity ice water or chiller fluid.

In addition, the vessel 36 has filtered air injected at the base to aerate the fluid in the vessel and to positively pressurize the vessel 36. Air may also be filtered and injected into the vessel 36 via a line 41 to aerate the media and to clear the inoculation tube 32.

Referring to FIG. 10, wherein like reference characters indicate like parts as above, a bioreactor for forming a mycelium product may be seeded. In this regard, warm media 42 that has not solidified is pumped into a vessel 36 mixing with colonized media 43 and displacing suspended tissue ready for inoculation.

As schematically illustrated, the warm media 42 is supplied from a supply tank 44 of tergazyme and a supply tank 45 of deionized water via a peristaltic pump 31 and inoculation tube 32 into the vessel 36. A sparger (not shown) is used to distribute the fluid.

Referring to FIG. 11, wherein like reference characters indicate like parts as above, the bioreactor may also have an inlet 46 in the line 42 for the delivery of a media and seed culture as well as a second peristaltic pump 31 for removing culture from the vessel 36 and a bypass line for the return of culture to the vessel 41. The two pumps 31 could be the two pumps on a Biostat B controller.

In this embodiment, the bioreactor (vessel 36) and tubing are charged with teragyzme, e.g. for 5 minutes, and then rinsed with deionized water. Media is then applied to fill one third of the vessel 36 to mix with residual water. Seed culture is then applied and the remainder of the media added.

During the process, the media and culture are blended with Ruston turbines.

In this embodiment, fully incubated media is recycled and blended to seed new media.

Referring to FIG. 13, multiple mycelium parts 47 may be made in accordance with the invention.

As indicated, the multiple parts 47 are cast simultaneously in a two-part mold 48, conveyed forward on a conveyor 49 and subsequently pushed into incubation vessels (not shown).

Each two part mold 48 has a pair of mold halves 50 that form a cavity when closed on each other. In addition, suitable ports are arranged in the mold 48 for the delivery of disinfected substrate 51 (e.g. a slurry of the broth material described above) into the mold cavity. Typically, filtered air is pumped intermittently to clear the work surface, i.e. the conveyor 49, and/or any infection tube and the slurry is pumped with a metering pump, such as, a peristaltic pump or a diaphragm pump.

The disinfected substrate 51 injected into a mold 48 may include a slurry of particles containing a tissue culture and/or a secondary chemical such as a gelatinizing agent. The substrate may be mechanically actuated to uniformly fill the mold cavity and/or modify the density. The substrate may also be compresses with a piston or vibrated into position.

Each mold 48 serves to cast the substrate slurry 51 into a solid part 47.

The parts 47 can be conveyed to an incubation vessel (not shown) that can control environmental conditions including but not limited to temperature $CO_2$, and relative humidity.

Referring to FIG. 13, a series of trays 52 may be conveyed along a conveyor 53 to receive media from a hopper 54 provided with a sliding gate 55 to allow intermittent dispensing of materials for making mycelium products.

In one embodiment, characterized as "Vibratory Filling: Casting Discrete profiles", the following sequence is performed:
1. a vibrator head is fitted with a template which contains a desired 2-dimensional profile which is affixed beneath the sliding gate 53.
2. a flat tray 50 with a lid clip bottom is advanced and interfaced with the 2-dimensional profile fully enclosing the cavity (gate on top, tray on bottom)
3. system vibrates, gate cycles, 2-dimensional profile is filled. Multiple gate cycles vary packing density and ensures the filling of a reverse drafted profile (smaller at top). Reverse drafting the profile allows the part to drop or slide out at end of cycle. Vibrating cycle may be 10-20 seconds.
4. gate closes. Seeing top of profile. Tray is then retraced to rail height with "cast" substrate incorporating geometry of 2-dimensional profile, flat top and bottom.
5. Tray advances with fully formed 2-dimensional profile
6. Tray is lidded
7. Tray is inoculated
8. Tray is processed (washed and part podded)
Or 9. Tray may go directly into dryer (no popping or washing). Requires metal or high temperature plastic tray material.

In this embodiment, the substrate is either a "mix" as above described with possible thickening agent (simple profile) of Agar inoculated. More complew profiles will require Agar or additional thickening agents.

In another embodiment, characterized as "3-D Filing", the cavity design of a tray is three dimensional. That is a 3-D cavity is created which feature an exterior profile with reverse drafted sides. Any desired features are suspended from the full surface of the mold and are drafted away from exterior walls. Sufficient gaps are created in the top face of the cavity such that when the assemblage is vibrated substrate will fall in between the gaps into the cavity. Suspension tabs are made this enough such that the depressions in part do not impact function.

In this embodiment, the following sequence is performed:
1. Flat tray is brought up against the 3-D cavity profile's open bottom
2. Cavity, hopper and tray are vibrated such that the material flows through into gaps in the 3-D cavity and fills under desired features and up to surface. Multiple gate closings may be necessary for optimal filling and compression.
3. Gate closes sealing top of 3-D cavity profile
4. Tray gently retracts leaving "cast" 3-D solid on flat tray
5. Incubate with lid or directly in pod Incubation can run with either a lidded flat tray (stage 1) in which case the parts are de-lidded and processed for drying, or filled parts are incubated directly on "drying" trays that then go directly in the oven.

There is now washing or cleaning. Trays go into a steamed pallet sized grow pad room and is moved directly into an oven.

Parts are removed. Pad plus tray are steamed and refilled.

In another embodiment, characterized as "3-D Filing Ejection/Die—molding" in order to free a part from the mold the following techniques may be used:
1. short vibration during removal
2. quickly cool and heat tool (freeze exterior of part, then heat tool rapidly to expand slightly, melting water will cause lubrication (ice/water/steel). If freeze first ¼ inch of substrate provide additional dimensional stability during movement. Little effect on growth.
3. Aggressive draft (6 degrees)
4. secondary "ejection stage" (using ejection plate).

In still another embodiment using cold ejection techniques, the following are of note:
Two components: cold steel contracts forcing material out of tool against draft angles)

Substrate surface freezes (expanding, pushing part out of tool) and creating stable "skin" for transport.

In heating stage, steel would expand quickly and lubricate surface.

May be possible to just keep fill head steel very cold (0° F.) and rely on substrate to substrate adhesion for easy demolding strength.

An ejection plate operation follows the following sequence:
1. after the hopper gate closes over the 3-D cavity the cavity and tool move downwards ½ inch
2. the ejection plate (inverse profile to that of the 3-d cavity opening) is the slide between the 3-D cavity and hopper bottom.
3. tray is then raised ¼ inch providing even pressure over fill areas (optionally or instead of, 3-D profile is raised pulling substrate into ejection plate, leaving substrate on flat tool bottom).

What is claimed is:
1. A process of producing a homogeneous polymer matrix comprising the steps of
growing a viable mycelium in a liquid suspension;
extracting mycelium from the liquid suspension;

thereafter incubating the mycelium for a period of time sufficient to induce mycelium cohesion and to form a solid homogeneous mass of mycelial chitin; and thereafter drying the solid material to remove moisture and to inactivate the mycelium.

2. A process as set forth in claim 1 wherein said step of growing includes growing mycelium on a scaffold immersed within said liquid suspension.

3. A process as set forth in claim 1 wherein said step of drying includes applying a salt solution to the solid material to impart electrical conductivity thereto.

4. A process as set forth in claim 1 wherein said step of drying includes adding NAOH to the solid material to impart an anti-fungal characteristic thereto.

5. A process as set forth in claim 1 wherein said step of extracting includes removing fragments of mycelium from the liquid suspension.

6. A process as set forth in claim 5 wherein said fragments are combined into a cohesive whole of three dimensional shape.

7. A process as set forth in claim 1 wherein said step of growing includes growing mycelium across the surface of a nutrient rich fluid to form a sheet.

8. A process as set forth in claim 7 further comprising the step of placing a scaffold in contact with said sheet to allow mycelium to colonize said scaffold.

9. A process as set forth in claim 7 wherein said step of extracting includes removing the sheet from the nutrient rich fluid in continuous form.

10. A process as set forth in claim 7 wherein said step of extracting includes passing a porous membrane material through the liquid suspension to allow mycelium to adhere and grow along the membrane material.

11. A process as set forth in claim 7 wherein said step of extracting includes removing the sheet from the nutrient rich fluid.

12. A process as set forth in claim 11 further comprising the steps of obtaining a plurality of said sheets, stacking said sheets and reanimating the mycelium of said sheets to fuse said sheets together to form a cohesive whole.

13. A process as set forth in claim 12 wherein said step of stacking said sheets includes interposing a plurality of textiles in alternating manner with said sheets.

14. A process as set forth in claim 12 wherein said step of incubating includes incubating said stacked sheets in an environment of 90% relative humidity and at a temperature of 86° F. for three days.

15. A process as set forth in claim 11 further comprising the steps of removing a plurality of cutouts of predetermined shape from said sheet, stacking said cutouts and reanimating the mycelium of said cutouts to fuse said cutouts together to form a cohesive whole.

16. A process as set forth in claim 15 further comprising the step of adding glycol to said stack of cutouts to plasticize the mycelium.

17. A process of producing a homogeneous polymer matrix comprising the steps of
growing a viable mycelium across the surface of a nutrient rich fluid in a liquid suspension to form a sheet of mycelium;
extracting the sheet of mycelium from the liquid suspension;
thereafter incubating the sheet of mycelium for a period of time sufficient to induce mycelium cohesion and to form a solid homogeneous mass of mycelial chitin; and
thereafter drying the solid material to remove moisture and to inactivate the mycelium.

18. A process as set forth in claim 17 further comprising the steps of
obtaining a plurality of said sheets, stacking said sheets and reanimating the mycelium of said sheets to fuse said sheets together to form a cohesive whole.

19. A process as set forth in claim 17 wherein said step of extracting includes passing a porous membrane material through the liquid suspension to allow mycelium to adhere and grow along the membrane material.

20. A process of producing a homogeneous polymer matrix comprising the steps of
growing a viable mycelium in a liquid suspension;
extracting fragments of mycelium from the liquid suspension;
combining said fragments into a cohesive whole of bulk three dimensional shape;
thereafter incubating the cohesive whole for a period of time sufficient to induce mycelium cohesion and to form a solid homogeneous mass of mycelial chitin; and
thereafter drying the solid material to remove moisture and to inactivate the mycelium.

\* \* \* \* \*